US00PP09977P

United States Patent [19]

Meier et al.

[11] Patent Number: Plant 9,977

[45] Date of Patent: Jul. 22, 1997

[54] BA 77-279 KENTUCKY BLUEGRASS

[75] Inventors: Virgil D. Meier, Marysville, Ohio; Jay B. Burr, S.E. Salem, Oreg.

[73] Assignee: OMS Investments, Inc., Wilmington, Del.

[21] Appl. No.: 604,763

[22] Filed: Feb. 23, 1996

[51] Int. Cl.[6] ..... A01H 5/00

[52] U.S. Cl. ..... Plt./90.2

[58] Field of Search ..... Plt./90.2

[56] References Cited

U.S. PATENT DOCUMENTS

| | | | |
|---|---|---|---|
| P.P. 3,156 | 5/1972 | Fuchigami et al. | Plt./90.2 |
| P.P. 3,186 | 5/1972 | Barenbrug et al. | Plt./90.2 |
| P.P. 4,336 | 11/1978 | Mayer et al. | Plt./90.2 |
| P.P. 6,280 | 9/1988 | Meier et al. | Plt./90.2 |
| P.P. 6,537 | 1/1989 | Meier et al. | Plt./90.2 |
| P.P. 6,538 | 1/1989 | Meier et al. | Plt./90.2 |
| P.P. 6,585 | 2/1989 | Meier et al. | Plt./90.2 |
| P.P. 7,831 | 3/1992 | Meier et al. | Plt./90.2 |
| P.P. 8,490 | 12/1993 | Meier et al. | Plt./90.2 |
| P.P. 9,036 | 1/1995 | Meier et al. | Plt./90.2 |
| P.P. 9,209 | 7/1995 | Meier et al. | Plt./90.2 |
| P.P. 9,611 | 7/1996 | Meier | Plt./90.2 |

*Primary Examiner*—James R. Feyrer

[57] ABSTRACT

A variety of Kentucky Bluegrass having a high level of resistane to leaf spot and melting out disease; a medium to high level of resistance to several rust diseases and dollar spot; a dark green color throughout the growing season; a good level of drought tolerance; high quality dense persistent turf formation under a wide variety of environmental conditions; and a medium level of seed yielding capacity.

1 Drawing Sheet

BACKGROUND OF THE INVENTION

1. Field of the Invention

The present invention relates to a new and distinct variety of *Poa pratensis* that has been designated Ba 77-279 Kentucky Bluegrass.

2. Description of Related Art

Kentucky bluegrasses have been disclosed in U.S. Pat. No. P.P. 3,156, issued May 9, 1972; U.S. Pat. No. P.P. 3,186, issued May 23, 1972; U.S. Pat. No. P.P. 4,336, issued Nov. 28, 1978; U.S. Pat. No. P.P. 6,280, issued Sep. 6, 1988; U.S. Pat. Nos. P.P. 6,538 and 6,538, issued on Jan. 17, 1989; U.S. Pat. No. P.P. 6,585, issued Feb. 7, 1989; U.S. Pat. No. P.P. 7,831, issued Mar. 17, 1992; U.S. Pat. No. P.P. 8,490, issued Dec. 7, 1993; U.S. Pat. No. P.P. 9,036, issued Jan. 3, 1995; U.S. Pat. No. P.P. 9,209, issued Jul. 18, 1995; and pending U.S. Plant patent applications Ser. No. 08/453,864, filed May 30, 1995, and Ser. No. 08/532,995, filed Sep. 22, 1995.

SUMMARY OF THE VARIETY

Ba 77-279 plant material originated by crossing Ba73-709, an unreleased Kentucky bluegrass plant maintained in the O. M. Scott plant nursery, as the seed parent with a Merion Kentucky bluegrass plant as the pollen parent. As a result of this breeding, a distinct variety was produced and asexually propagated by rhizomes, tillers and disseminules.

Seed of Ba 77-279 Kentucky Bluegrass was produced first at Marysville, Ohio and later at Gervais, Oreg. This seed was used to plant turf performance evaluation trials and later seed production fields. Asexual production of Ba 77-279 by propagules (tillers and rhizomes) and by disseminules (modified caryopses produced by apomixis) has consistently produced progeny plants indistinguishable from the mother plant. The apomixis level of Ba 77-279 is approximately 89% based upon examining seedling characeristics of approximately 100 to 150 seedlings from different crop years in a growth chamber.

Ba 77-279 has a number of highly desirable characteristics including a high level of resistance to Drechslera spp. that causes leaf spot, melting out and crown rot; a medium to high level of resistance to Puccinia spp. that causes several types of rust infections and *Schlerotinia homoeocarpa* that causes dollar spot. Ba 77-279 has an attractive leafy turf growth habit; moderately wide leaf blades and an attractive dark green color which can be maintained throughout the entire growing season. Ba 77-279 demonstrates good drought tolerance and excellent turf performance as evidenced by consistently high scores for quality, color and density. Ba 77-279 has a medium seed yield potential in the bluegrass seed production region of the northwestern U.S.

In comparison with a number of other bluegrass varieties, Ba 77-279 is average for seed size, number of whorls per panicle, vegetative leaf width, and ligule length. Ba 77-279 is below average in panicle length and width, number of florets per spikelet, flag leaf and vegetative leaf length and width, peduncle length and width, culm length and lemma hair content. Ba 77-279 is above average in spikelet width.

In comparison to many other varieties, Ba 77-279 is significantly greater in rachella length, spikelet length, flag leaf ligule length and internode length. Ba 77-279 has significantly less number of branches per whorl in the panicle, number of nodes in the culm and vegetative leaf ligule hair content as compared with other Bluegrass varieties. In comparison to most varieties, Ba 77-279 is significantly greater in outer and inner glume length and flag leaf thickness. Ba 77-279 is much darker green than either of its parents (Ba73-709 and Merion).

DETAILED DESCRIPTION OF THE VARIETY

Figure 1:
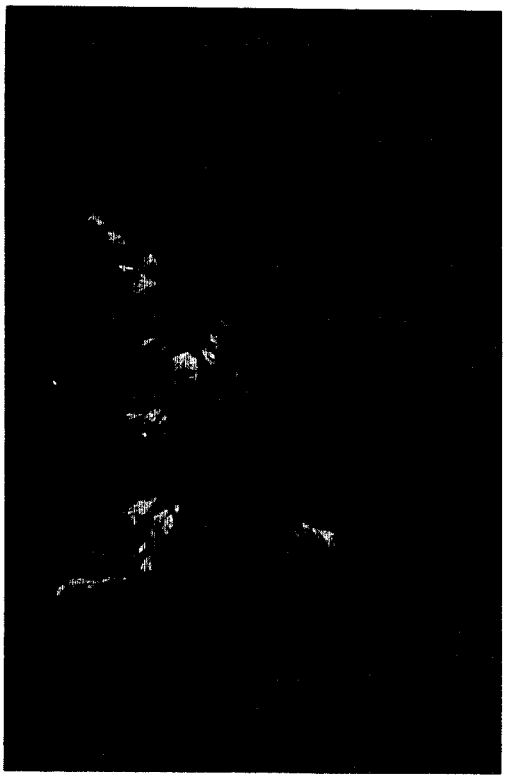
FIG. 1 is a Ba 77-279 Kentucky Bluegrass panicle.
Figure 3:
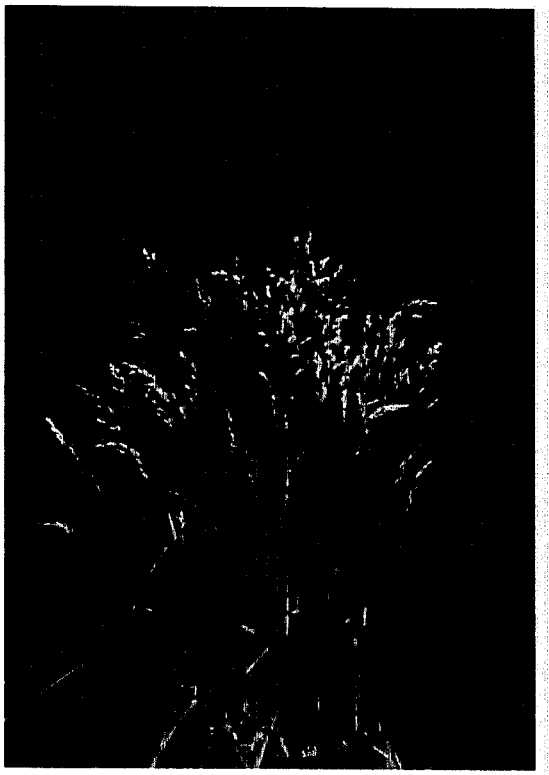
FIG. 3 is a Ba 77-279 Kentucky Bluegrass plant shortly after completing anthesis.
Figure 2:
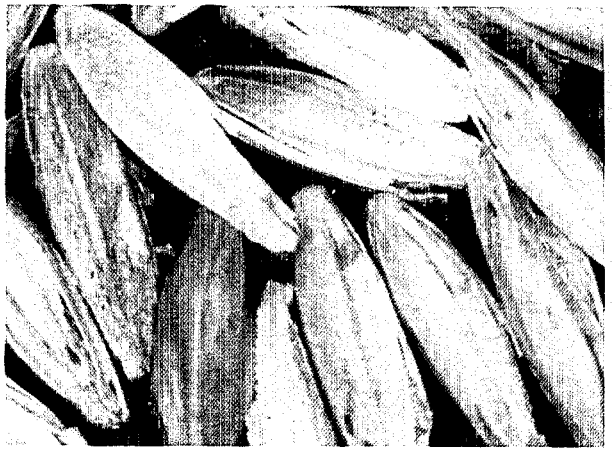
FIG. 2 is a Ba 77-279 Kentucky Bluegrass seed.

Ba 77-279 Kentucky Bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60°–80° F.), culms are erect averaging 36.3 cm in length and 3.0 nodes per culm and the uppermost internode averages 12.7 cm in length. The peduncle averages 20.0 cm in length and 0.64 mm in width. The flag leaf averages 4.7 cm in length, 3.5 mm in width and 0.29 mm in thickness and the ligule 1.5 mm in length. The vegetative leaf averages 17.4 cm in length, 3.4 mm in width, 0.345 mm in thickness and a ligule length of 0.22 mm.

The panicle averages 77.1 mm in length, 66.0 mm in width, and 9.2 whorls. The lowest whorl averages 2.3 branches and the third whorl from the button of the panicle average 2.1 branches. A spikelet in the lowest whorl averages 5.4 mm in length, 2.6 mm in width, 3.1 florets and the outer glume and inner glume average 3.7 and 4.1 mm in length, respectively. A spikelet from the third whorl from the bottom of the panicle is 5.3 mm in length, 2.9 mm in width, 3.1 florets, and the outer glume and inner glume averages 3.7 and 4.0 mm in length, respectively.

The conditioned seed of Ba 77-279 averages 2.99 mm in length, 0.85 mm in width, and a rachilla length of 0.82 mm. The seed count for Ba 77-279 averages approximately 1,039,000 seeds per pound.

Comparisions of Ba 77-279 with other Kentucky Bluegrass varieties in terms of seed dimension and seed numbers per pound are shown in Tables 1 and 2 as follows:

TABLE 1

Morphological Comparison of Seed and Rachilla Measurements and Lemma Hair of Ba 77-279 and Other Kentucky Bluegrass Varieties at Marysville, OH After Conditioning

| | Seed | | | |
|---|---|---|---|---|
| Variety | Length mm | Width mm | Rachilla mm | Lemma* Hair |
| Ba 77-279 | 2.99 | .85 | .82 | 3.4 |
| Ba 74-114 | 3.23 | 0.89 | 0.88 | 4.2 |
| Ba 73-366 | 3.04 | 0.91 | 0.80 | 4.4 |
| Ba 73-381 | 3.00 | 0.94 | 0.86 | 4.9 |
| Abbey | 2.97 | 0.89 | 0.80 | 3.8 |
| Adelphi | 2.70 | 0.84 | 0.65 | 4.4 |
| America | 2.40 | 0.68 | 0.68 | 2.8 |
| Baron | 3.08 | 0.81 | 0.71 | 5.0 |
| Bristol | 2.94 | 0.88 | 0.73 | 4.3 |
| Chateau | 2.81 | 0.86 | 0.71 | 4.5 |
| Coventry | 2.71 | 0.81 | 0.70 | 4.0 |
| Eclipse | 2.77 | 0.83 | 0.68 | 3.5 |
| Georgetown | 2.94 | 0.82 | 0.74 | 4.9 |
| Gnome | 2.78 | 0.83 | 0.75 | 4.1 |
| Kelly | 3.07 | 0.89 | 0.75 | 4.2 |
| Marquis | 2.97 | 0.87 | 0.83 | 4.7 |
| Midnight | 2.94 | 0.76 | 0.78 | 5.7 |
| Nassau | 3.07 | 0.86 | 0.68 | 3.4 |
| Ram I | 3.23 | 0.89 | 0.80 | 6.0 |
| Touchdown | 2.93 | 0.88 | 0.71 | 4.6 |
| Victa | 3.00 | 0.80 | 0.82 | 3.5 |
| LSD (.05) | 0.16 | 0.05 | 0.13 | 0.86 |

*Rating Scale: 0–9; 9 = abundant row of hairs

TABLE 2

Comparison of Seed Numbers Per Pound of Ba 77-279 and Other Kentucky Bluegrass Varieties at Marysville, OH After Conditioning

| Variety | Seeds Per Pound |
|---|---|
| Ba 77-279 | 1,039,000 |
| Ba 74-114 | 978,000 |
| Ba 73-366 | 1,025,586 |

TABLE 2-continued

Comparison of Seed Numbers Per Pound of Ba 77-279 and Other Kentucky Bluegrass Varieties at Marysville, OH After Conditioning

| Variety | Seeds Per Pound |
|---|---|
| Ba 73-381 | 1,171,000 |
| Abbey | 1,003,037 |
| Adelphi | 1,383,976 |
| America | 1,659,824 |
| Baron | 1,051,693 |
| Bristol | 1,270,821 |
| Chateau | 1,300,105 |
| Coventry | 1,246,200 |
| Eclipse | 1,335,668 |
| Georgetown | 1,431,000 |
| Gnome | 1,017,641 |
| Kelly | 921,166 |
| Marquis | 1,054,642 |
| Midnight | 1,227,000 |
| Nassau | 1,127,130 |
| Ram I | 1,214,000 |
| Touchdown | 1,211,000 |
| Victa | 1,038,298 |

Ba 77-279 differs significantly morphologically from many other Kentucky Bluegrass varieties in regard to the following characteristics: (1) seed length; (2) rachilla length; (3) panicle length; (4) number of branches in the whorl; (5) spikelet length and width; (6) glume length and width; (7) culm length and internode length; (8) flag leaf thickness; and (9) vegetative leaf with and sheath color.

Since environmental conditions such as soil and climate may influence morphological characteristics to some extent, comparisions of morphological characteristics of Ba 77-279 were made with other Kentucky Bluegrass varieties and the comparisons are set forth in the following Tables 3–8:

TABLE 3

Morphological Comparison of Panicles, Whorl Number and Whorl Branches of Ba 77-279 and Other Kentucky Bluegrass Varieties in the Greenhouse at Marysville, OH

| | Panicles | | | | Number of Branches | |
|---|---|---|---|---|---|---|
| Variety | Nodding* | Length mm | Width mm | Whorl Number | Lowest Whorl | Third Whorl |
| Ba 77-279 | 2.4 | 77.1 | 66.0 | 9.2 | 2.3 | 2.1 |
| Ba 74-114 | 2.0 | 88.8 | 62.0 | 9.3 | 2.1 | 2.1 |
| Ba 73-366 | 1.6 | 88.8 | 68.4 | 8.8 | 4.3 | 3.7 |
| Ba 73-381 | 1.1 | 80.2 | 55.3 | 9.8 | 4.1 | 3.9 |
| Abbey | 1.6 | 80.4 | 59.3 | 9.3 | 3.8 | 3.3 |
| Adelphi | 1.8 | 106.8 | 76.4 | 10.0 | 3.6 | 3.0 |
| America | 2.3 | 67.7 | 51.1 | 8.8 | 3.3 | 3.5 |
| Baron | 2.2 | 92.6 | 71.0 | 10.0 | 3.4 | 2.8 |
| Bristol | 2.0 | 85.5 | 61.5 | 8.4 | 2.8 | 2.7 |
| Chateau | 2.9 | 65.2 | 57.3 | 8.5 | 3.3 | 2.8 |
| Coventry | 2.5 | 64.0 | 54.2 | 8.4 | 3.3 | 2.5 |
| Eclipse | 1.3 | 89.2 | 74.0 | 10.7 | 3.3 | 2.1 |
| Georgetown | 1.0 | 80.0 | 57.0 | 7.4 | 2.1 | 2.6 |
| Gnome | 1.1 | 80.6 | 56.0 | 10.6 | 4.6 | 3.9 |
| Kelly | 2.0 | 88.0 | 70.2 | 9.8 | 4.6 | 3.7 |
| Marquis | 1.1 | 82.0 | 63.0 | 10.3 | 3.9 | 3.6 |
| Midnight | 2.0 | 75.8 | 48.4 | 7.1 | 2.9 | 3.0 |
| Nassau | 2.2 | 91.2 | 68.6 | 10.0 | 2.5 | 2.1 |
| Ram I | 1.3 | 67.7 | 47.0 | 7.3 | 3.0 | 3.2 |
| Touchdown | 1.1 | 73.1 | 75.0 | 7.6 | 2.1 | 2.3 |
| Victa | 1.7 | 74.9 | 58.3 | 10.0 | 4.7 | 3.5 |
| LSD (.05) | 0.68 | 7.35 | 8.62 | 0.66 | 0.72 | 0.50 |

*Rate Scale: 1–9; 9 = most nodding

TABLE 4

Morphological Comparison of Spikelets and Florets of Ba 77-279 and Other Kentucky Bluegrass Varieties in the Greenhouse at Marysville, OH

| | Spikelet* | | | | Number of Florets | |
|---|---|---|---|---|---|---|
| | Lowest Whorl | | Third Whorl | | Per Spikelet | |
| Variety | Length mm | Width mm | Length mm | Width mm | Lowest Whorl | Third Whorl |
| Ba 77-279 | 5.4 | 2.6 | 5.3 | 2.9 | 3.1 | 3.1 |
| Ba 74-114 | 5.6 | 3.2 | 5.6 | 3.3 | 4.1 | 4.1 |
| Ba 73-366 | 4.6 | 2.5 | 4.7 | 2.6 | 2.6 | 2.8 |
| Ba 73-381 | 4.7 | 2.4 | 4.6 | 2.6 | 2.7 | 2.7 |
| Abbey | 4.4 | 2.2 | 4.5 | 2.2 | 3.0 | 3.0 |
| Adelphi | 4.6 | 2.2 | 4.8 | 2.2 | 4.4 | 4.4 |
| America | 4.6 | 2.2 | 4.4 | 2.3 | 4.5 | 4.3 |
| Baron | 5.4 | 2.8 | 5.4 | 3.1 | 4.0 | 4.2 |
| Bristol | 4.9 | 2.4 | 5.0 | 2.5 | 4.2 | 4.5 |
| Chateau | 4.4 | 2.4 | 4.4 | 2.4 | 3.4 | 3.5 |
| Coventry | 4.4 | 2.2 | 4.5 | 2.4 | 3.2 | 3.5 |
| Eclipse | 4.6 | 2.4 | 4.6 | 2.4 | 3.6 | 3.6 |
| Georgetown | 5.0 | 2.3 | 5.0 | 2.6 | 4.8 | 4.9 |
| Gnome | 4.6 | 2.5 | 4.6 | 2.9 | 3.2 | 3.2 |
| Kelly | 5.1 | 2.5 | 5.2 | 2.8 | 3.7 | 3.8 |
| Marquis | 4.3 | 2.2 | 4.4 | 2.3 | 3.1 | 2.9 |
| Midnight | 5.3 | 2.5 | 5.5 | 2.4 | 4.4 | 4.7 |
| Nassau | 4.7 | 2.6 | 4.8 | 3.0 | 4.2 | 4.3 |
| Ram I | 5.4 | 2.6 | 5.3 | 2.8 | 3.6 | 3.4 |
| Touchdown | 5.1 | 2.9 | 4.8 | 2.8 | 4.1 | 4.0 |
| Victa | 4.5 | 2.5 | 4.5 | 2.4 | 3.3 | 3.2 |
| LSD (.05) | 0.41 | 0.35 | 0.38 | 0.35 | 0.58 | 0.53 |

*Microscope measurements

TABLE 5

Morphological Comparison of Glumes of Ba 77-279 and Other Kentucky Bluegrass Varieties in the Greenhouse at Marysville, OH

| | Glume Length (mm) | | | | Glume Hairs* | | | |
|---|---|---|---|---|---|---|---|---|
| | Outer | | Inner | | Lowest Whorl | | Third Whorl | |
| Variety | Lowest Whorl | Third Whorl | Lowest Whorl | Third Whorl | Outer | Inner | Outer | Inner |
| Ba 77-279 | 3.7 | 3.7 | 4.1 | 4.0 | 2.1 | 3.0 | 2.0 | 2.3 |
| Ba 74-114 | 3.5 | 3.3 | 3.9 | 3.8 | 2.6 | 3.2 | 2.2 | 2.8 |
| Ba 73-366 | 2.8 | 2.8 | 3.2 | 3.1 | 1.7 | 1.3 | 1.3 | 2.0 |
| Ba 73-381 | 2.8 | 2.9 | 3.2 | 3.1 | 1.7 | 2.3 | 2.1 | 2.3 |
| Abbey | 2.7 | 2.7 | 3.1 | 3.1 | 0.6 | 0.9 | 1.0 | 1.0 |
| Adelphi | 2.7 | 2.6 | 3.0 | 3.1 | 0.6 | 2.7 | 1.1 | 1.9 |
| America | 2.1 | 2.1 | 2.5 | 2.5 | 0.2 | 0.5 | 0.3 | 0.3 |
| Baron | 3.1 | 3.2 | 3.6 | 3.7 | 4.8 | 4.4 | 4.2 | 4.6 |
| Bristol | 2.8 | 3.0 | 3.3 | 3.4 | 1.0 | 2.2 | 0.8 | 2.2 |
| Chateau | 2.8 | 2.9 | 3.1 | 3.2 | 1.5 | 2.6 | 2.0 | 1.8 |
| Coventry | 2.7 | 2.8 | 3.1 | 3.1 | 1.5 | 2.7 | 1.6 | 2.4 |
| Eclipse | 3.0 | 3.0 | 3.4 | 3.4 | 1.5 | 1.9 | 1.8 | 1.9 |
| George-town | 2.8 | 2.8 | 3.1 | 3.1 | 1.7 | 2.7 | 1.2 | 2.4 |
| Gnome | 2.8 | 2.9 | 3.3 | 3.3 | 1.0 | 1.9 | 1.2 | 1.6 |
| Kelly | 3.0 | 3.1 | 3.4 | 3.5 | 1.3 | 1.5 | 1.1 | 0.8 |
| Marquis | 2.8 | 2.7 | 3.1 | 3.1 | 0.9 | 1.1 | 1.7 | 1.8 |
| Midnight | 2.6 | 2.6 | 3.0 | 3.1 | 1.8 | 2.8 | 1.0 | 2.4 |
| Nassau | 2.6 | 2.7 | 2.9 | 3.0 | 2.1 | 2.6 | 4.2 | 4.4 |
| Ram I | 2.9 | 3.0 | 3.6 | 3.5 | 1.1 | 2.3 | 0.7 | 1.2 |
| Touch-down | 3.3 | 3.3 | 3.8 | 3.8 | 0.7 | 2.1 | 1.1 | 1.4 |
| Victa | 2.8 | 2.7 | 3.1 | 3.1 | 0.8 | 1.1 | 1.1 | 1.3 |
| LSD (.05) | 0.23 | 0.22 | 0.22 | 0.23 | 0.9 | 0.9 | 0.9 | 0.9 |

*Rating Scale: 0–9; 9 = many hairs

TABLE 6

Morphological Comparison of Flag Leaves of Ba 77-279 and Other Kentucky Bluegrass Varieties in the Greenhouse at Marysville, OH

| Variety | Length cm | Width mm | Thickness mm | Leaf Angle[1/] | Leaf Curve[2/] | Ligule mm |
|---|---|---|---|---|---|---|
| Ba 77-279 | 4.7 | 3.5 | 0.29 | 2.1 | 4.5 | 1.5 |
| Ba 74-114 | 5.3 | 3.4 | 0.23 | 1.4 | 5.0 | 1.2 |
| Ba 73-366 | 4.5 | 3.6 | 0.18 | 5.1 | 4.4 | 1.5 |
| Ba 73-381 | 4.3 | 3.5 | 0.22 | 1.9 | 5.0 | 1.3 |
| Abbey | 3.8 | 3.4 | 0.14 | 2.7 | 4.1 | 1.3 |
| Adelphi | 5.7 | 3.4 | 0.18 | 5.2 | 5.0 | 1.1 |
| America | 4.3 | 2.6 | 0.21 | 4.6 | 5.0 | 0.6 |
| Baron | 7.0 | 4.2 | 0.15 | 9.2 | 4.4 | 1.2 |
| Bristol | 4.3 | 3.2 | 0.21 | 2.3 | 5.0 | 0.6 |
| Chateau | 4.0 | 2.7 | 0.19 | 3.4 | 2.0 | 0.9 |
| Coventry | 3.7 | 3.0 | 0.14 | 0.7 | 4.3 | 0.9 |
| Eclipse | 3.9 | 3.2 | 0.19 | 8.7 | 5.0 | 1.1 |
| Georgetown | 5.7 | 2.8 | 0.22 | 1.9 | 5.0 | 0.6 |
| Gnome | 4.5 | 3.5 | 0.18 | 4.3 | 5.0 | 0.8 |
| Kelly | 4.8 | 4.1 | 0.18 | 3.1 | 4.4 | 1.5 |
| Marquis | 5.5 | 3.6 | 0.24 | 2.7 | 4.6 | 0.8 |
| Midnight | 3.8 | 2.6 | 0.19 | 1.1 | 5.0 | 0.4 |
| Nassau | 6.0 | 3.7 | 0.19 | 5.9 | 4.7 | 1.1 |
| Ram I | 3.4 | 3.1 | 0.19 | 1.0 | 4.8 | 0.7 |
| Touchdown | 4.1 | 2.7 | 0.16 | 3.4 | 4.1 | 1.1 |
| Victa | 3.9 | 3.7 | 0.27 | 2.1 | 4.6 | 1.3 |
| LSD (.05) | 1.0 | 0.42 | 0.025 | 2.50 | 0.40 | 0.17 |

| | Hairs[3/] | | |
|---|---|---|---|
| Variety | Leaf Margin | Ligule | Sheath Color[4/] |
| Ba 77-279 | 0.6 | 0.7 | 0.9 |
| Ba 74-114 | 0.5 | 2.1 | 1.8 |
| Ba 73-366 | 0.4 | 2.2 | 0.5 |
| Ba 73-381 | 0.4 | 3.6 | 1.5 |
| Abbey | 0.8 | 1.6 | 0.2 |
| Adelphi | 1.8 | 1.6 | 0.4 |
| America | 0.4 | 0.7 | 1.9 |
| Baron | 1.0 | 3.8 | 2.6 |
| Bristol | 0.4 | 1.9 | 2.0 |
| Chateau | 1.1 | 3.1 | 0.3 |
| Coventry | 0.8 | 1.7 | 2.0 |
| Eclipse | 1.0 | 1.0 | 0.2 |
| Georgetown | 0.6 | 2.0 | 2.0 |
| Gnome | 0.9 | 3.2 | 1.5 |
| Kelly | 1.1 | 2.5 | 2.2 |
| Marquis | 0.5 | 3.8 | 1.5 |
| Midnight | 0.4 | 0.3 | 2.0 |
| Nassau | 2.6 | 2.4 | 0.8 |
| Ram I | 0.5 | 1.3 | 2.0 |
| Touchdown | 1.0 | 1.0 | 7.7 |
| Victa | 1.0 | 0.8 | 0.5 |
| LSD (.05) | 0.47 | 0.70 | 0.76 |

[1/]Degrees from the stem
[2/]Rating Scale: 1–9; 1 = curves up; 5 = no curve; 9 = curves down
[3/]Rating Scale: 0–9; 0 = none; 9 = many
[4/]Rating Scale: 0–9; 0 = no color; 9 = dark purple

TABLE 7

Morphological Comparison of Peduncles, Culms, Node Numbers Per Culm and Internode Length of Ba 77-279 and Other Kentucky Bluegrass Varieties in the Greenhouse at Marysville, OH

| Variety | Peduncle Length cm | Peduncle Width mm | Culm Length cm | Nodes Per Culm | Top Internode Length cm |
|---|---|---|---|---|---|
| Ba 77-279 | 20.0 | 0.64 | 36.3 | 3.0 | 12.7 |
| Ba 74-114 | 24.7 | 0.71 | 44.9 | 3.7 | 13.4 |
| Ba 73-366 | 26.4 | 0.70 | 42.7 | 4.1 | 9.2 |
| Ba 73-381 | 24.3 | 0.81 | 39.5 | 3.1 | 10.8 |
| Abbey | 23.2 | 0.65 | 41.3 | 4.1 | 11.0 |

TABLE 7-continued

Morphological Comparison of Peduncles, Culms, Node Numbers Per Culm and Internode Length of Ba 77-279 and Other Kentucky Bluegrass Varieties in the Greenhouse at Marysville, OH

| Variety | Peduncle Length cm | Peduncle Width mm | Culm Length cm | Nodes Per Culm | Top Internode Length cm |
|---|---|---|---|---|---|
| Adelphi | 24.5 | 0.66 | 40.0 | 4.0 | 10.4 |
| America | 16.2 | 0.62 | 31.8 | 3.1 | 11.0 |
| Baron | 34.0 | 0.70 | 52.8 | 4.2 | 12.8 |
| Bristol | 22.9 | 0.73 | 43.5 | 4.0 | 12.6 |
| Chateau | 20.7 | 0.61 | 38.9 | 4.4 | 9.9 |
| Coventry | 19.6 | 0.49 | 34.7 | 4.5 | 7.9 |
| Eclipse | 23.7 | 0.66 | 39.2 | 4.9 | 9.9 |
| Georgetown | 21.7 | 0.68 | 37.5 | 3.2 | 11.1 |
| Gnome | 19.4 | 0.84 | 35.3 | 3.1 | 9.2 |
| Kelly | 29.4 | 0.75 | 46.6 | 3.6 | 11.8 |
| Marquis | 27.1 | 0.83 | 34.1 | 3.4 | 7.8 |
| Midnight | 20.5 | 0.72 | 29.5 | 2.8 | 7.6 |
| Nassau | 25.0 | 0.66 | 36.0 | 3.9 | 7.4 |
| Ram I | 22.2 | 0.69 | 30.5 | 2.5 | 6.6 |
| Touchdown | 23.6 | 0.52 | 38.0 | 4.0 | 8.4 |
| Victa | 21.2 | 0.81 | 37.9 | 3.7 | 10.3 |
| LSD (.05) | 3.17 | 0.077 | 3.32 | 0.44 | 1.94 |

TABLE 8

Morphological Comparison of Vegetative Leaves of Ba 77-279 and Other Kentucky Bluegrass Varieties in the Greenhouse at Marysville, OH

| Variety | Length cm | Width mm | Thickness mm | Leaf Angle[1/] | Leaf Curve[2/] |
|---|---|---|---|---|---|
| Ba 77-279 | 17.4 | 3.4 | 0.34 | 67.9 | 5.5 |
| Ba 74-114 | 18.9 | 4.5 | 0.36 | 50.9 | 5.0 |
| Ba 73-366 | 22.9 | 3.8 | 0.40 | 53.0 | 7.1 |
| Ba 73-381 | 22.1 | 3.3 | 0.30 | 62.5 | 8.2 |
| Abbey | 20.7 | 3.6 | 0.28 | 51.3 | 7.4 |
| Adelphi | 19.4 | 3.7 | 0.28 | 67.0 | 4.6 |
| America | 21.4 | 3.1 | 0.32 | 66.0 | 6.4 |
| Baron | 18.2 | 4.3 | 0.29 | 35.0 | 4.4 |
| Bristol | 18.2 | 3.7 | 0.32 | 65.5 | 6.9 |
| Chateau | 23.1 | 3.3 | 0.33 | 39.7 | 5.4 |
| Coventry | 23.4 | 3.6 | 0.25 | 63.0 | 7.3 |
| Eclipse | 20.3 | 4.4 | 0.30 | 65.5 | 5.4 |
| Georgetown | 19.5 | 3.6 | 0.29 | 56.7 | 5.8 |
| Gnome | 18.2 | 2.9 | 0.29 | 43.2 | 6.6 |
| Kelly | 22.8 | 3.9 | 0.30 | 55.5 | 7.0 |
| Marquis | 19.7 | 3.7 | 0.38 | 46.4 | 7.8 |
| Midnight | 19.5 | 3.5 | 0.31 | 63.3 | 5.0 |
| Nassau | 16.3 | 3.7 | 0.29 | 63.2 | 4.9 |
| Ram I | 19.1 | 3.6 | 0.27 | 70.8 | 6.5 |
| Touchdown | 16.7 | 3.7 | 0.24 | 51.3 | 4.0 |
| Victa | 21.5 | 3.6 | 0.36 | 56.3 | 6.7 |
| LSD (.05) | 3.50 | 0.43 | 0.044 | 15.90 | 1.54 |

| Variety | Ligule Length mm | Hairs[3/] Leaf Ligule | Hairs[3/] Leaf Margin | Sheath Roughness[4/] | Sheath Color[5/] |
|---|---|---|---|---|---|
| Ba 77-279 | 0.22 | 1.5 | 2.0 | 8.8 | 0.2 |
| Ba 74-114 | 0.14 | 3.3 | 2.6 | 8.7 | 2.0 |
| Ba 73-366 | 0.23 | 5.2 | 4.2 | 8.5 | 0.0 |
| Ba 73-381 | 0.16 | 3.2 | 0.7 | 8.2 | 2.0 |
| Abbey | 0.32 | 4.4 | 2.8 | 7.7 | 0.0 |
| Adelphi | 0.34 | 2.6 | 3.4 | 8.8 | 0.0 |
| America | 0.12 | 1.7 | 2.1 | 8.4 | 2.0 |
| Baron | 0.33 | 4.6 | 3.6 | 7.4 | 0.4 |
| Bristol | 0.12 | 2.6 | 3.0 | 8.9 | 2.0 |
| Chateau | 0.22 | 3.3 | 3.1 | 7.8 | 0.5 |
| Coventry | 0.32 | 3.1 | 2.4 | 8.1 | 0.3 |
| Eclipse | 0.38 | 2.8 | 2.6 | 9.0 | 0.2 |
| Georgetown | 0.14 | 2.5 | 2.4 | 8.5 | 2.0 |

TABLE 8-continued

| | | | | | |
|---|---|---|---|---|---|
| Gnome | 0.23 | 1.6 | 0.8 | 7.5 | 1.4 |
| Kelly | 0.34 | 4.6 | 2.4 | 8.8 | 0.0 |
| Marquis | 0.21 | 3.6 | 1.1 | 6.8 | 1.1 |
| Midnight | 0.10 | 1.3 | 1.6 | 7.7 | 2.0 |
| Nassau | 0.34 | 2.5 | 3.3 | 8.5 | 1.4 |
| Ram I | 0.09 | 1.8 | 2.0 | 7.7 | 2.0 |
| Touchdown | 0.29 | 1.4 | 1.3 | 7.9 | 8.0 |
| Victa | 0.26 | 2.3 | 1.7 | 7.9 | 0.1 |
| LSD (.05) | 0.045 | 0.79 | 0.70 | 0.89 | 0.57 |

[1/]Degrees from the stem
[2/]Rating Scale: 1–9; 1 = curves up; 5 = no curve; 9 = curves down
[3/]Rating Scale: 0–9; 0 = none; 9 = many
[4/]Rating Scale: 1–9; 1 = rough; 9 = smooth
[5/]Rating Scale: 0–9; 0 = no color; 9 = dark purple color Ba 77-279 has been an outstanding performer as exhibited by high turf quality ratings and dark green color at a number of locations across the U.S. in comparison to other Kentucky Bluegrass varieties. With regard to a comparataive analysis conducted for purposes of determining color of Ba 77-279 plants relative to other Kentucky Bluegrass varieties, readings were taken of the vegetative color of Ba 77-279 during mid-May while the turf was actively growing with adequate nutrient and water availability. The readings were taken in full sun with several actively growing leaves being compared, one at a time, utilizing color chips from the Munsell Book of Color as a reference. On this basis, the color of Ba 77-279 was determined to be 7.5 GY 4/4. During the same time period, the color of similar leaves of other Kentucky Bluegrass varieties were determined by the same procedure to be as follows: Ba 74-114 — 7.5 GY 4/4; Ba 73-381 — 5 GY 4/4; Ba 73-366 — 5 GY 4/4; Ba 73-540 — 5 GY 4/4; Abbey — 5 GY 3/4; and Coventry — 5 GY 4/4. However, it should be noted that the general apparent color of turf does not always correlate directly with the color of the individual actively growing leaves within the turf and that turf color varies with nutrient level and time of year with some varieties being darker or lighter green depending on such factors.

Ba 77-279 demonstrates a dark green color which can be maintained throughout the growing season. It also has a medium wide leaf, good density and seedling vigor. Comparisons of Ba 77-279 with other Kentucky bluegrass varieties for quality, color, density and seedling vigor are set forth hereinafter in Tables 9–13:

TABLE 9

A Comparison of Quality of Ba 77-279 and Other Kentucky Bluegrass Varieties In Three Tests Conducted at Nineteen (19) Locations in the U.S. in Three Tests Conducted.

| Variety | Test (Annual Means) A | B | C |
|---|---|---|---|
| Ba 77-279 | 6.1 | 6.4 | 5.9 |
| Ba 73-366 | 5.5 | 5.5 | 5.3 |
| Ba 73-381 | 5.4 | 5.6 | 5.3 |
| Ba 74-114 | 5.3 | 5.6 | 5.1 |
| Abbey | 5.5 | 5.5 | 5.3 |
| Able I | 5.8 | 6.1 | 5.9 |
| A-34 | 5.6 | 5.7 | 5.5 |
| Banff | 6.0 | 5.9 | 5.4 |
| Baron | 5.8 | 5.7 | 5.3 |
| Classic | 5.8 | 5.9 | 5.4 |
| Coventry | 5.9 | 6.0 | 5.7 |
| Eclipse | 5.9 | 6.2 | 6.0 |
| Estate | 5.9 | 5.9 | 5.6 |

TABLE 9-continued

A Comparison of Quality of Ba 77-279 and Other Kentucky Bluegrass Varieties In Three Tests Conducted at Nineteen (19) Locations in the U.S. in Three Tests Conducted.

| | Test (Annual Means) | | |
|---|---|---|---|
| Variety | A | B | C |
| Georgetown | 5.9 | 5.9 | 5.4 |
| Glade | 6.2 | 6.0 | 5.6 |
| Gnome | 5.5 | 5.5 | 5.3 |
| Haga | 5.9 | 5.8 | 5.5 |
| Kelly | 5.5 | 5.4 | 5.2 |
| Kenblue | 4.6 | 4.5 | 4.3 |
| Marquis | 5.4 | 5.5 | 5.4 |
| Merion | 4.2 | 4.8 | 4.9 |
| Merit | 5.4 | 5.5 | 5.3 |
| Midnight | 6.2 | 6.4 | 6.3 |
| Monopoly | 5.3 | 5.5 | 5.3 |
| Nassau | 5.6 | 5.8 | 5.2 |
| Ram I | 6.1 | 5.9 | 5.4 |
| South Dakota | 4.1 | 4.2 | 4.2 |
| Touchdown | 5.5 | 5.9 | 5.5 |
| LSD (.05) | 0.3 | 0.2 | 0.2 |

Rating Scale: 1–9; 9 = ideal turf

TABLE 10

A Comparison of Genetic Color of Ba 77-279 and Other Kentucky Bluegrass Varieties in Three Tests (A–C) Conducted at Ten (10) Locations in the US

| | TESTS (Annual Means) | | |
|---|---|---|---|
| Variety | A | B | C |
| Ba 77-279 | 6.9 | 6.8 | 7.2 |
| Ba 74-114 | 7.0 | 7.2 | 7.2 |
| Ba 73-366 | 5.5 | 5.5 | 5.9 |
| Ba 73-381 | 6.0 | 5.7 | 6.4 |
| Abbey | 5.6 | 5.9 | 5.8 |
| Able I | 6.6 | 6.8 | 6.8 |
| A-34 | 5.0 | 5.4 | 4.6 |
| Banff | 5.1 | 6.0 | 5.5 |
| Baron | 6.0 | 6.0 | 5.9 |
| Classic | 5.2 | 5.9 | 5.2 |
| Coventry | 5.9 | 5.6 | 5.8 |
| Eclipse | 6.3 | 6.6 | 6.4 |
| Estate | 5.8 | 5.3 | 5.3 |
| Georgetown | 5.2 | 6.1 | 5.3 |
| Glade | 6.7 | 6.3 | 6.7 |
| Gnome | 6.0 | 6.1 | 5.8 |
| Haga | 5.1 | 5.8 | 5.3 |
| Kelly | 5.6 | 5.7 | 6.1 |
| Kenblue | 4.6 | 5.0 | 5.3 |
| Marquis | 6.1 | 6.1 | 6.4 |
| Merion | 5.7 | 5.8 | 5.4 |
| Merit | 5.7 | 5.7 | 6.2 |
| Midnight | 7.1 | 7.3 | 7.7 |
| Monopoly | 4.8 | 4.9 | 4.8 |
| Nassau | 6.0 | 6.6 | 6.5 |
| Ram I | 6.7 | 5.9 | 6.6 |
| South Dakota | 4.5 | 4.8 | 4.7 |
| Touchdown | 5.5 | 5.5 | 5.3 |
| LSD (.05) | 0.5 | 0.4 | 0.7 |

Rating Scale: 1–9; 9 = dark green.

TABLE 11

A Comparison of Fall Density of Ba 77-279 and Other Kentucky Bluegrass Varieties at Martinsville, New Jersey

| Variety | Fall Density |
|---|---|
| Ba 77-279 | 7.0 |
| Ba 73-366 | 5.3 |
| Ba 73-381 | 5.3 |
| Ba 74-114 | 5.7 |
| Abbey | 4.7 |
| Able I | 4.7 |
| A-34 | 5.7 |
| Banff | 6.3 |
| Baron | 5.7 |
| Classic | 6.3 |
| Coventry | 6.0 |
| Eclipse | 5.3 |
| Estate | 5.0 |
| Georgetown | 6.7 |
| Glade | 5.7 |
| Gnome | 6.0 |
| Haga | 6.7 |
| Kelly | 5.0 |
| Kenblue | 5.0 |
| Marquis | 5.7 |
| Merion | 3.7 |
| Merit | 5.3 |
| Midnight | 7.3 |
| Monopoly | 5.0 |
| Nassau | 5.3 |
| Ram I | 6.7 |
| South Dakota | 3.0 |
| Touchdown | 5.7 |
| LSD (.05) | 1.4 |

Ratings Scale: 1–9; 9 = maximum density

TABLE 12

A Comparison of Leaf Texture of Ba 77-279 and Other Kentucky Bluegrass Varieties at Martinsville, NJ.

| Variety | Leaf Texture |
|---|---|
| BA 77-279 | 5.3 |
| Ba 74-114 | 4.0 |
| Ba 73-366 | 4.3 |
| Ba 73-381 | 4.0 |
| Abbey | 5.0 |
| Able I | 5.7 |
| A-34 | 4.3 |
| Banff | 5.3 |
| Baron | 5.0 |
| Classic | 5.3 |
| Coventry | 5.0 |
| Eclipse | 5.7 |
| Estate | 4.3 |
| Georgetown | 6.0 |
| Glade | 5.0 |
| Gnome | 5.3 |
| Haga | 5.7 |
| Kelly | 4.3 |
| Kenblue | 6.0 |
| Marquis | 4.3 |
| Merion | 4.0 |
| Merit | 4.7 |
| Midnight | 6.7 |
| Monopoly | 5.0 |
| Nassau | 5.0 |
| Ram I | 5.0 |
| South Dakota | 3.7 |
| Touchdown | 5.3 |
| LSD (.05) | 0.9 |

Rating Scale: 1–9; 9 = very fine

TABLE 13

A Comparison of Seedling Vigor of Ba 77-279 and Other Kentucky Bluegrass Varieties at Six Locations in the the U.S. and Canada*

| Variety | Seedling Vigor Mean |
|---|---|
| Ba 77-279 | 6.2 |
| Ba 73-366 | 6.3 |
| Ba 73-381 | 6.3 |
| Ba 74-114 | 5.3 |
| Abbey | 6.4 |
| Able I | 6.3 |
| A-34 | 6.0 |
| Banff | 7.7 |
| Baron | 6.7 |
| Classic | 7.1 |
| Coventry | 6.1 |
| Eclipse | 6.1 |
| Estate | 6.1 |
| Georgetown | 7.0 |
| Glade | 6.7 |
| Gnome | 6.3 |
| Haga | 7.1 |
| Kelly | 6.6 |
| Kenblue | 7.4 |
| Marquis | 6.3 |
| Merion | 2.6 |
| Merit | 6.4 |
| Midnight | 5.4 |
| Monopoly | 7.1 |
| Nassau | 6.4 |
| Ram I | 6.5 |
| South Dakota | 6.7 |
| Touchdown | 5.8 |
| LSD (.05) | 0.7 |

Rating Scale: 1–9; 9 = Maximum vigor
Locations: Fort Collins, CO; Post Falls, ID; North Brunswick, NJ; Adelphi, NJ; Richmond Hill, Ontario; pooled data from Halsey, Hubbard and Gervais, OR.

Turf diseases are one of the major causes of inconsistent and poor turf performance. Ba 77-279 has been found to have a high level of resistance to leaf spot and melting out caused by *Drechslera poae* (formerly called *Helminthosporium vagans*). Ba 77-279 furthermore has been found to have a medium to high level of resistance to dollar spot caused by *Sclerotinia homoecarpa* and to several rust diseases caused by Puccinia spp.

Comparisons of disease incidence of Ba 77-279 as compared with other Kentucky Bluegrass varieties in regard to leaf spot, dollar spot, and rusts, are presented in Tables 14–18.

TABLE 14

A Comparison of Leaf Spot Incidence in Ba 77-279 and Other Kentucky Bluegrass Varieties in Two (2) Tests Conducted at Seven (7) Locations in the U.S.

| | Means | |
|---|---|---|
| Variety | Test 1* | Test 2** |
| Ba 77-279 | 6.0 | 7.4 |
| Ba 73-366 | 4.3 | 5.1 |
| Ba 73-381 | 2.0 | 5.8 |
| Ba 74-114 | 4.7 | 6.8 |
| Abbey | 4.7 | 5.1 |
| Able I | 6.0 | 7.1 |
| A-34 | 4.7 | 5.4 |
| Banff | 4.7 | 5.9 |
| Baron | 4.0 | 5.4 |
| Classic | 3.3 | 5.4 |
| Coventry | 3.7 | 5.8 |
| Eclipse | 6.3 | 7.4 |

TABLE 14-continued

A Comparison of Leaf Spot Incidence in Ba 77-279 and Other Kentucky Bluegrass Varieties in Two (2) Tests Conducted at Seven (7) Locations in the U.S.

| | Means | |
|---|---|---|
| Variety | Test 1* | Test 2** |
| Estate | 4.0 | 5.9 |
| Georgetown | 6.0 | 6.3 |
| Glade | 3.0 | 4.8 |
| Gnome | 3.7 | 5.7 |
| Haga | 3.7 | 5.9 |
| Kelly | 4.7 | 5.1 |
| Kenblue | 1.7 | 1.8 |
| Marquis | 3.7 | 5.6 |
| Merion | 7.3 | 7.3 |
| Merit | 4.3 | 5.4 |
| Midnight | 5.7 | 6.6 |
| Monopoly | 4.3 | 5.2 |
| Nassau | 4.3 | 6.2 |
| Ram I | 4.3 | 4.9 |
| South Dakota | 1.0 | 1.8 |
| Touchdown | 5.3 | 6.3 |
| LSD (.05) | 1.5 | 0.7 |

Rating Scale: 1–9; 9 = no disease
*Locations: Pooled data from Halsey, Hubbard and Gervais, OR.
**Locations: Post Falls, ID; North Brunswick and Adelphia, NJ; Marysville, OH LSD

TABLE 15

A Comparison of Dollar Spot Disease Incidence of Ba 77-279 and Other Kentucky Bluegrass Varieties in Three (3) Tests Conducted at Five (5) Locations in the U.S.

| | Means | | |
|---|---|---|---|
| Variety | Test A[1] | Test B[2] | Test C[3] |
| Ba 77-279 | 8.3 | 7.8 | 7.0 |
| Ba 73-366 | 8.3 | 7.1 | 6.2 |
| Ba 73-381 | 7.3 | 6.6 | 6.4 |
| Ba 74-114 | 8.3 | 7.9 | 4.8 |
| Abbey | 8.0 | 6.8 | 6.3 |
| Able I | 8.3 | 6.8 | 6.1 |
| A-34 | 7.7 | 6.7 | 6.0 |
| Banff | 7.7 | 6.4 | 6.2 |
| Baron | 7.7 | 6.9 | 6.8 |
| Classic | 8.0 | 7.4 | 6.3 |
| Coventry | 7.7 | 5.9 | 5.9 |
| Eclipse | 8.3 | 7.5 | 7.2 |
| Estate | 8.3 | 5.3 | 5.6 |
| Georgetown | 8.0 | 6.9 | 6.1 |
| Glade | 7.7 | 7.0 | 6.4 |
| Gnome | 8.0 | 6.7 | 6.1 |
| Haga | 7.7 | 6.3 | 6.2 |
| Kelly | 8.0 | 7.3 | 6.3 |
| Kenblue | 8.0 | 6.8 | 6.8 |
| Marquis | 8.0 | 6.8 | 6.7 |
| Merion | 7.7 | 6.9 | 6.1 |
| Merit | 8.0 | 6.8 | 6.7 |
| Midnight | 8.3 | 8.0 | 6.6 |
| Monopoly | 8.0 | 7.1 | 6.7 |
| Nassau | 8.0 | 7.4 | 6.7 |
| Ram I | 7.3 | 6.0 | 4.9 |
| South Dakota | 8.0 | 7.3 | 5.8 |
| Touchdown | 8.0 | 6.8 | 6.1 |
| LSD (.05) | 0.9 | 1.1 | 0.8 |

Rating Scale: 1–9; 9 = no disease
[1]Locations: Kingston, RI
[2]Locations: Urbana, IL; Adelphia, NJ; Kingston, RI; Haymarket, VA
[3]Locations: Urbana, IL; Silver Spring, MD; Kingston, RI

TABLE 16

A Comparison of Stem Rust Disease Incidence in Ba 77-279 and Other Kentucky Bluegrass Varieties at Kingston, R.I.

| Variety | Stem Rust |
|---|---|
| Ba 77-279 | 7.3 |
| Ba 73-366 | 6.7 |
| Ba 73-381 | 7.3 |
| Ba 74-114 | 5.7 |
| Abbey | 7.0 |
| Able I | 3.3 |
| A-34 | 4.3 |
| Banff | 7.7 |
| Baron | 7.0 |
| Classic | 8.0 |
| Coventry | 6.7 |
| Eclipse | 4.0 |
| Estate | 6.3 |
| Georgetown | 8.7 |
| Glade | 7.7 |
| Gnome | 7.0 |
| Haga | 8.0 |
| Kelly | 8.0 |
| Kenblue | 5.7 |
| Marquis | 6.7 |
| Merion | 1.0 |
| Merit | 6.3 |
| Midnight | 8.0 |
| Monopoly | 6.3 |
| Nassau | 8.0 |
| Ram I | 8.0 |
| South Dakota | 4.3 |
| Touchdown | 2.3 |
| LSD (.05) | 1.4 |

Rating Scale: 1–9; 9 = no disease

TABLE 17

A Comparison of Leaf Rust Disease Incidence in Ba 77-279 and Other Kentucky Bluegrass Varieties at Kingston, R.I.

| Variety | Leaf Rust |
|---|---|
| Ba 77-279 | 6.0 |
| Ba 74-114 | 6.7 |
| Ba 73-366 | 5.7 |
| Ba 73-381 | 6.3 |
| Abbey | 6.3 |
| Able I | 7.0 |
| A-34 | 6.0 |
| Banff | 7.0 |
| Baron | 8.3 |
| Classic | 8.7 |
| Coventry | 7.0 |
| Eclipse | 5.7 |
| Estate | 6.3 |
| Georgetown | 7.7 |
| Glade | 7.0 |
| Gnome | 6.7 |
| Haga | 7.0 |
| Kelly | 5.0 |
| Kenblue | 6.7 |
| Marquis | 6.3 |
| Merion | 2.3 |
| Merit | 6.0 |
| Midnight | 6.0 |
| Monopoly | 5.3 |
| Nassau | 7.0 |
| Ram I | 6.7 |
| South Dakota | 6.7 |
| Touchdown | 3.7 |
| LSD (.05) | 2.4 |

Rating Scale: 1–9; 9 = no disease

TABLE 18

A Comparison of Stripe Rust Disease Incidence in Ba 77-279 and Other Kentucky Bluegrass Varieties in Tests Conducted at Three Locations[1/] in Oregon

| Variety | Stripe Rust |
|---|---|
| Ba 77-279 | 6.0 |
| Ba 74-114 | 6.7 |
| Ba 73-366 | 5.0 |
| Ba 73-381 | 4.7 |
| Abbey | 4.3 |
| Able I | 6.0 |
| A-34 | 5.0 |
| Banff | 6.0 |
| Baron | 6.0 |
| Classic | 6.3 |
| Coventry | 5.0 |
| Eclipse | 6.0 |
| Estate | 5.7 |
| Georgetown | 6.3 |
| Glade | 3.0 |
| Gnome | 4.7 |
| Haga | 6.3 |
| Kelly | 5.0 |
| Kenblue | 3.3 |
| Marquis | 5.3 |
| Merion | 3.7 |
| Merit | 5.0 |
| Midnight | 4.7 |
| Monopoly | 5.3 |
| Nassau | 5.3 |
| Ram I | 6.0 |
| South Dakota | 4.0 |
| Touchdown | 3.0 |
| LSD (.05) | 1.2 |

Rating Scale: 1–9; 9 = no disease

[1/]Pooled data from Halsey, Hubbard and Gervais, Oregon.

Ba 77-279 has shown good drought tolerance and has a medium seed yielding capability. Comparisons for drought tolerance and seed yields of Ba 77-279 with other Kentucky Bluegrass are presented in Table 19–20.

TABLE 19

A Comparison of Drought Tolerance of Ba 77-279 and Other Kentucky Bluegrass Varieties at Carbondale, IL.

| Variety | Drought Tolerance |
|---|---|
| Ba 77-279 | 5.0 |
| Ba 73-366 | 3.0 |
| Ba 73-381 | 2.0 |
| Ba 74-114 | 3.0 |
| Abbey | 3.7 |
| Able I | 4.0 |
| A-34 | 4.0 |
| Banff | 4.7 |
| Baron | 3.0 |
| Classic | 3.7 |
| Coventry | 4.3 |
| Eclipse | 4.0 |
| Estate | 4.7 |
| Georgetown | 4.0 |
| Glade | 3.7 |
| Gnome | 3.3 |
| Haga | 4.0 |
| Kelly | 2.7 |
| Kenblue | 2.7 |
| Marquis | 3.3 |

TABLE 19-continued

A Comparison of Drought Tolerance of Ba 77-279 and Other Kentucky Bluegrass Varieties at Carbondale, IL.

| Variety | Drought Tolerance |
|---|---|
| Merion | 3.7 |
| Merit | 2.7 |
| Midnight | 4.3 |
| Monopoly | 2.7 |
| Nassau | 3.3 |
| Ram I | 4.7 |
| South Dakota | 2.7 |
| Touchdown | 4.7 |
| LSD (.05) | 1.6 |

Rating Scale: 1–9; 9 = no dormancy

TABLE 20

A Comparison of Seed Yield in Pounds Per Acre of Ba 77-279 and Coventry Kentucky Bluegrass In Two (2) Tests Conducted at Gervais, Oregon.

| | Test A | Test B |
|---|---|---|
| Ba 77-279 | 672 | 382 |
| Coventry | 568 | 425 |
| LSD (.05) | 162 | 97 |

What is claimed is:

1. A variety of Kentucky Bluegrass plant, substantially as shown and described, characterized by a high level of resistance to leaf spot and melting out disease; a medium to high level of resistance to several rust diseases and dollar spot; a dark green color throughout the growing season; a good level of drought tolerance; high quality dense persistent turf formation under a wide variety of environmental conditions; and a medium level of seed yielding capacity.

* * * * *